(12) United States Patent
Várkuti

(10) Patent No.: US 11,918,818 B2
(45) Date of Patent: *Mar. 5, 2024

(54) NEURONAL SIGNAL SYSTEM, METHOD AND COMPUTER PROGRAM FOR DEVICE STATUS SIGNALING

(71) Applicant: CereGate GmbH, Hamburg (DE)

(72) Inventor: Bálint Várkuti, Munich (DE)

(73) Assignee: CEREGATE GMBH, Munich (DE)

( * ) Notice: Subject to any disclaimer, the term of this patent is extended or adjusted under 35 U.S.C. 154(b) by 169 days.

This patent is subject to a terminal disclaimer.

(21) Appl. No.: 17/672,024

(22) Filed: Feb. 15, 2022

(65) Prior Publication Data

US 2022/0168582 A1 Jun. 2, 2022

Related U.S. Application Data

(63) Continuation of application No. 16/663,807, filed on Oct. 25, 2019, now Pat. No. 11,260,235.

(30) Foreign Application Priority Data

Sep. 26, 2019 (DE) .......................... 102019214752.6

(51) Int. Cl.
  *A61N 1/372* (2006.01)
  *A61N 1/05* (2006.01)
  *A61N 1/378* (2006.01)

(52) U.S. Cl.
  CPC ....... *A61N 1/37252* (2013.01); *A61N 1/0529* (2013.01); *A61N 1/37217* (2013.01); *A61N 1/378* (2013.01)

(58) Field of Classification Search
  CPC ................ A61N 1/372; A61N 1/37211; A61N 1/37217; A61N 1/37252; A61N 1/37254; A61N 1/37258
  See application file for complete search history.

(56) References Cited

U.S. PATENT DOCUMENTS

| | | |
|---|---|---|
| 4,441,202 A | 4/1984 | Tong et al. |
| 4,445,512 A | 5/1984 | Krupka et al. |

(Continued)

FOREIGN PATENT DOCUMENTS

| | | |
|---|---|---|
| DE | 102019202666 A1 | 8/2020 |
| DE | 102019209096 A1 | 12/2020 |

(Continued)

OTHER PUBLICATIONS

Anderson D.N., et al., "Optimized Programming Algorithm for Cylindrical and Directional Deep Brain Stimulation Electrodes," Journal of Neural Engineering, IOP Publishing Limited, Jan. 24, 2018, 19 pages, URL: https://doi.org/10.1088/1741-2552/aaa14b.

(Continued)

*Primary Examiner* — Brian T Gedeon
(74) *Attorney, Agent, or Firm* — Kowert, Hood, Munyon, Rankin & Goetzel, P.C.

(57) ABSTRACT

The present invention relates to a system for communicating an operational state of a neuronal stimulation apparatus to an individual, comprising: means for determining the operational state of the apparatus; means for transmitting a first neuronal stimulation signal to a neuronal stimulation means of the individual adapted to elicit a sensory percept in the cortex of the individual, wherein the first neuronal stimulation signal is indicative of the operational state of the apparatus. The present invention further relates to a method and computer program comprising the steps of: determining the operational state of the apparatus, transmitting a neuronal stimulation signal to a neuronal stimulation means of the individual adapted to elicit a sensory percept in the cortex of the individual, wherein the first neuronal stimulation signal is indicative of the determined operational state of the apparatus.

25 Claims, 8 Drawing Sheets

(56) References Cited

U.S. PATENT DOCUMENTS

| | | |
|---|---|---|
| 4,488,555 A | 12/1984 | Imran |
| 5,800,535 A | 9/1998 | Howard, III |
| 6,400,989 B1 | 6/2002 | Eckmiller |
| 7,751,884 B2 | 7/2010 | Ternes et al. |
| 7,774,056 B2 | 8/2010 | Torgerson |
| 8,193,766 B2 | 6/2012 | Rondoni et al. |
| 8,290,596 B2 | 10/2012 | Wei et al. |
| 8,352,029 B2 | 1/2013 | Ternes et al. |
| 8,364,271 B2 | 1/2013 | De Ridder |
| 8,380,314 B2 | 2/2013 | Panken et al. |
| 8,423,145 B2 | 4/2013 | Pless et al. |
| 8,437,858 B2 | 5/2013 | Dapper et al. |
| 8,475,172 B2 | 7/2013 | Lieberman et al. |
| 8,494,633 B2 | 7/2013 | Tobacman |
| 8,509,904 B2 | 8/2013 | Rickert et al. |
| 8,812,128 B2 | 8/2014 | Kothandaraman |
| 9,095,314 B2 | 8/2015 | Osorio et al. |
| 9,314,190 B1 | 4/2016 | Giuffrida et al. |
| 9,357,938 B2 | 6/2016 | Ang et al. |
| 9,526,896 B2 | 12/2016 | Greenberg et al. |
| 9,636,497 B2 | 5/2017 | Bradley et al. |
| 9,713,720 B2 | 7/2017 | Zhu |
| 9,974,478 B1 | 5/2018 | Brokaw et al. |
| 10,543,359 B2 | 1/2020 | Giftakis et al. |
| 10,568,559 B2 | 2/2020 | Parker et al. |
| 2003/0065366 A1 | 4/2003 | Merritt et al. |
| 2004/0267152 A1 | 12/2004 | Pineda |
| 2006/0129205 A1 | 6/2006 | Boveja et al. |
| 2006/0241717 A1 | 10/2006 | Whitehurst et al. |
| 2006/0241718 A1 | 10/2006 | Tyler et al. |
| 2007/0027397 A1 | 2/2007 | Fischell et al. |
| 2007/0250134 A1 | 10/2007 | Miesel et al. |
| 2008/0129517 A1 | 6/2008 | Crosby et al. |
| 2008/0139954 A1 | 6/2008 | Day et al. |
| 2009/0082829 A1 | 3/2009 | Panken et al. |
| 2009/0264789 A1 | 10/2009 | Molnar et al. |
| 2009/0306741 A1 | 12/2009 | Hogle et al. |
| 2010/0057161 A1 | 3/2010 | Machado et al. |
| 2010/0094382 A1 | 4/2010 | Pezaris et al. |
| 2010/0249879 A1 | 9/2010 | Bracker et al. |
| 2013/0150914 A1 | 6/2013 | Kelly et al. |
| 2013/0253299 A1 | 9/2013 | Weber et al. |
| 2014/0081348 A1 | 3/2014 | Fischell |
| 2014/0379046 A1 | 12/2014 | Tcheng et al. |
| 2015/0018724 A1 | 1/2015 | Hsu et al. |
| 2015/0073492 A1 | 3/2015 | Kilgard et al. |
| 2015/0290453 A1 | 10/2015 | Tyler et al. |
| 2016/0022992 A1 | 1/2016 | Franke et al. |
| 2016/0121118 A1 | 5/2016 | Franke et al. |
| 2017/0182328 A1 | 6/2017 | Moffitt |
| 2018/0050198 A1 | 2/2018 | Mazanec et al. |
| 2019/0030338 A1 | 1/2019 | Wu et al. |
| 2020/0269049 A1 | 8/2020 | Varkuti |

FOREIGN PATENT DOCUMENTS

| | | |
|---|---|---|
| EP | 2552304 B1 | 9/2015 |
| EP | 3229893 A1 | 10/2017 |
| EP | 3431138 A1 | 1/2019 |
| EP | 2486897 B1 | 5/2019 |
| JP | 2016540594 A | 12/2016 |
| KR | 20170132055 A | 12/2017 |
| KR | 101841625 B1 | 5/2018 |
| WO | 2012003451 A2 | 1/2012 |
| WO | 2012003451 A3 | 4/2014 |
| WO | 2016116397 A1 | 7/2016 |
| WO | 2018057667 A1 | 3/2018 |
| WO | 2018109715 A1 | 6/2018 |
| WO | 2020174051 A1 | 9/2020 |

OTHER PUBLICATIONS

Beauchamp M.S., et al., "Dynamic Electrical Stimulation of Sites in Visual Cortex Produces Form Vision in Sighted and Blind Humans," bioRxiv preprint, Nov. 5, 2018, 24 pages, Retrieved from the Internet: URL: http://dx.doi.org/10.1101/462697.

Donati A.R.C., et al., "Long Term Training with a Brain-Machine Interface Based Gait Protocol Induces Partial Neurological Recovery in Paraplegic Patients," 2016, Scientific Reports 6, Article 30383, 16 pages, Retrieved from the Internet: URL: https://doi.org/10.1038/srep30383.

First Office Action dated Mar. 17, 2020 for German Application No. DE102019209096.6, 8 pages.

First Office Action dated Oct. 16, 2019 for German Application No. DE102019202666.4, 16 pages.

Ghai S., et al., "Effect of Rhythmic Auditory Cueing on Parkinsonian Gait: A Systematic Review and Meta-Analysis," Nature Scientific Reports, Jan. 11, 2018, vol. 8, Article 506, DOI: 10.1038/s41598-017-16232-5, 19 pages.

Heming E., et al., "Designing a Somatosensory Neural Prosthesis: Percepts Evoked by Different Patterns of Thalamic Stimulation," Journal of Neural Engineering, Dec. 1, 2010, vol. 7 (6), 7 pages.

Heming E.A., et al., "Designing a Thalamic Somatosensory Neural Prosthesis: Consistency and Persistence of Percepts Evoked by Electrical Stimulation," IEEE Transactions on Neural Systems and Rehabilitation Engineering, IEEE Service Center, New York, US, Oct. 1, 2011, vol. 19 (5), pp. 477-482.

International Preliminary Report issued in International Application No. PCT/EP2020/055156, dated Sep. 10, 2021, 17 pages.

International Search report and Written Opinion issued in International Application No. PCT/EP2020/055156, dated Jul. 21, 2020, 22 pages.

Invitation to Pay Additional Fees and Where Applicable Protest Fee and Partial International Search for PCT/EP2020/055156, dated May 29, 2020, 21 pages.

Lee B., et al., "Engineering Artificial Somatosensation Through Cortical Stimulation in Humans," Frontiers in Systems Neuroscience, Jun. 4, 2018, vol. 12, Article 24, 11 pages, www.frontiersin.org.

Office Action for European Application No. 20200707624, dated Dec. 7, 2021, 14 pages.

Roelfsema P.R., et al., "Mind Reading and Writing: The Future of Neurotechnology," Trends in Cognitive Sciences, Elsevier Limited, May 6, 2018, 14 pages, Retrieved from URL: https://doi.org/10.1016/j.tics.2018.04.001.

Rosenthal L., et al., "Sensory Electrical Stimulation Cueing May Reduce Freezing of Gait Episodes in Parkinson's Disease," Hindawi Journal of Healthcare Engineering, 2018, Article ID 4684925, 6 pages.

Swan B.D., et al., "Sensory Percepts Induced by Microwire Array and DBS Microstimulation in Human Sensory Thalamus," Brain Stimulation, Elsevier Incorporated, 2018, vol. 11 (2), pp. 416-422, Retrieved from URL: https://doi.org/10.1016/j.brs.2017.10.017.

Yadav A.P., et al., "A Brain to Spine Interface for Transferring Artificial Sensory Information," 2020, Scientific Reports 10, Article 900, 2020, 15 pages.

Examination Report for German Application No. 1020192014752.6, dated Jun. 16, 2020, 8 pages.

Examination Report for German Application No. 102020210676.2, dated Apr. 16, 2021, 5 pages.

First Office Action for the German Application No. DE102020213417 dated May 31, 2021, 30 pages.

Notice of Reasons for Rejection for Japanese Patent Application No. 2021-550308, dated May 30, 2023, 4 pages.

Zhao F.J., et al., "A Review on Human Body Communication: Signal Propagation Model, Communication Performance, and Experimental Issues," Wireless Communications and Mobile Computing, Oct. 22, 2017, vol. 2017, 15 pages.

NEURONAL SIGNAL SYSTEM, METHOD AND COMPUTER PROGRAM FOR DEVICE STATUS SIGNALING

PRIORITY CLAIM

This Application is a continuation of U.S. patent application Ser. No. 16/663,807, titled "Neuronal Signal System, Method and Computer Program for Device Status Signaling", filed Oct. 25, 2019, which claims priority to German Patent Application number DE 102019214752.6, titled "Neuronal Signal System, Method and Computer Programm for Device Status Signaling", filed Sep. 26, 2019, which are hereby incorporated by reference in their entirety, as though fully and completely set forth herein.

The claims in the instant application are different than those of the parent application and/or other related applications. The Applicant therefore rescinds any disclaimer of claim scope made in the parent application and/or any predecessor application in relation to the instant application. Any such previous disclaimer and the cited references that it was made to avoid, may need to be revisited. Further, any disclaimer made in the instant application should not be read into or against the parent application and/or other related applications.

FIELD OF THE INVENTION

The present invention relates to a signal and data processing system, a method and a computer program for providing neuronal stimulation signals to an individual that may be used for signaling or communicating a device status to the individual.

DESCRIPTION OF THE RELATED ART

Similar to cardiac pacemakers, symptoms of neurological diseases such as Parkinson's disease (PD), essential tremor and dystonia are routinely treated via stimulation of the nervous system of the affected patients. For instance, deep brain stimulation (DBS) systems send electrical impulses through implanted electrodes to specific areas/nuclei of the brain to treat such symptoms. In the treatment of PD symptoms, these nuclei may include the globus pallidus interna, the thalamus and/or the subthalamic nucleus. It is known that DBS of the globus pallidus interna for instance improves motor function while DBS of the thalamus reduces tremor. Further, DBS of the subthalamic nucleus is associated with reduction in conventional PD medication.

Similar to the treatment of PD symptoms, electric stimulation devices can also be used for cardiac rhythm management, for treatment of Alzheimer's disease, dementia or depression as well as for communication purposes and implementations computer-brain interfaces.

For instance, U.S. Pat. No. 8,352,029 B2 relates to a method for implementing a neural stimulation therapy mode in an implantable medical device comprising the steps of mapping respective device states, defined by a neural event timer or indications of sensed physiologic events, to associated device actions in a stored neural table, storing an event represented as a device status word and a time stamp in a queue in response to an action input, and comparing current timer states or the indications of sensed physiologic events to a device state in the neural table and, if found to match, causing performance of associated device actions, wherein the device actions may neural stimulation energy delivery and/or a change in the timer states.

Similarly, U.S. Pat. No. 7,751,884 relates to an implantable medical device comprising stimulation circuitry adapted to provide neural stimulation energy to a neural stimulation electrode, one or more timers, including at least one neural event timer, a device behavior memory including a neural table, and a comparison circuit. The neural table maps a particular device state defined at least in part by a neural event timer to one or more associated device actions that include a neural stimulation energy delivery and/or a change in state of at least one neural event timer. The comparison circuit is adapted to compare a current state of the timers to a device state in the neural table and, if found to match, causing performance of one or more associated device actions.

Further, U.S. Pat. No. 8,812,128 relates to a rechargeable implantable medical device having a power source and being configured for monitoring the power source, generating a battery status signal based on the monitoring and configured for transcutaneously transmitting a communication signal and the battery status signal to an external device. The external device is configured for receiving the communication signal and the battery status signal from the rechargeable implantable medical device, changing from a low energy consumption state to a high energy consumption state in response to the received communication signal, and for generating a user-discernible signal in response to the received status signal.

Moreover, U.S. Pat. No. 8,193,766 relates to a system for estimating a time to recharge a rechargeable power source of an implantable medical device. A plurality of measured parameters relating to the implantable medical device and an external charging device are applied to a model of recharging performance and an estimate is provided to a patient, in advance of charging. Once charging has begun, updated estimates can be provided until charging is complete. Once charging is complete, the model may be updated to reflect any differences in the estimated time to complete charging and the actual time required to complete charging. The model may be based on limitations to the rate at which charge may be transferred to the rechargeable power source over a plurality of intervals.

However, typically, the stimulation parameters employed by such medical stimulation devices are selected or configured such that the treated patient does not directly perceive whether his device is properly operating or not. For instance, devices such as implanted electric stimulation devices may be powered by a limited power source such as a battery that may gradually discharge over time. At some point the charging level of the battery may be insufficient for the stimulation device to work properly.

Similarly, such devices may also stop working due to hardware failure (e.g. caused by strong external magnetic fields), or physiological changes of the treated brain areas that receive the stimulation treatment.

In many cases, however, the patient does not or at least not immediately realize that his therapy device is no longer operating properly, in particular, if the device does not comprise a configuration or status interface that can be accessed by the patient himself but only by trained medical personal. Even if the device comprises such an interface that is accessible by the patient (e.g. a wireless remote control or telemetry device) there might be situations (e.g. long holidays, an empty battery of the remote control etc.) when the patient cannot access the interface and obtain device status information.

In such situations, the neurological symptoms normally treated by the respective therapy device may gradually worsen, which may also remain undetected by the patient for a prolonged period of time. This may be particularly problematic if the neurostimulation device is used for treatment of psychological conditions such as dementia, Alzheimer's disease, schizophrenia, bipolar disorder and/or depression.

In such cases, a deactivation of the therapy device (e.g. caused by a low-battery or a false emergency deactivation caused by an external magnetic field) has no immediately perceivable effect and the patient will eventually only notice the undesired deactivation of his therapy device after a long time period when the untreated symptoms have already deteriorated substantially.

The present invention provides a simple, versatile and robust solution to some of the problems discussed above. Moreover, the present invention provides an efficient and generic way for signaling various types of device status information to users of present and future neuronal communication systems and/or brain-computer interface devices.

SUMMARY OF THE INVENTION

The above-mentioned problems are at least partly solved by the subject matter of the independent claims of the present application. Exemplary embodiments of the invention are the subject of the depended claims.

In one embodiment, the present invention provides a system for communicating an operational state of a neuronal stimulation apparatus to an individual, comprising: means for determining the operational state of the apparatus, means for transmitting a first neuronal stimulation signal to a neuronal stimulation means of the individual adapted to elicit a sensory percept in the cortex of the individual, wherein the first neuronal stimulation signal is indicative of the operational state of the apparatus.

In this way, a neuronal stimulation apparatus can be enabled to communicate various operational status information directly to the consciousness of a person using the apparatus without relying on additional interface equipment such as a remote control or a telemetry device. Consequently, the user or patient can directly be informed when the performance of the apparatus deteriorates or is about to deteriorate.

For instance, the operational state of the apparatus that is indicated to the individual may comprises one or more of the following:
  a. a fault state of the apparatus;
  b. a charging state of a power source of the apparatus;
  c. a normal operation state of the apparatus;
  d. a maintenance state of the apparatus;
  e. a connectivity state of the apparatus;
  f. a communication state of the apparatus
  g. a power transfer state between the apparatus and an external charging device.

For instance, in some embodiments, the system may be configured to inform the user/patient of a low battery state of the apparatus, before the battery charge level drops below a threshold value required for proper functioning of the apparatus. In this way the user can duly schedule a replacement or recharging of the battery, without risking his symptoms to become untreated. For instance, the system could be configured such that the device sends out a sequence of patient-perceptible somatosensory experiences (paresthesias) to alert the patient of the low-battery state (e.g. by inducing a feeling of vibration alternating between the left and the right hand of the patient) essentially providing a patient-internal alert which manifests as physical sensations.

Further, if the neuronal stimulation apparatus is a neuronal communication apparatus or a brain-computer interface device, the user can for instance be informed when a wireless signal quality deteriorates or increases and/or when a communication interface of the apparatus has received a message or information to be presented to the user.

Similarly, if the neuronal stimulation apparatus and/or its power source (such as a battery) may be implanted subcutaneously, the operational state may comprise a power transfer state between the apparatus and an external charging device. Such an external charging device may be configured to charge the power source of the apparatus wirelessly e.g. via electromagnetic induction. For instance, the means for determining the operational state of the apparatus may determine a relative position between the external charging device and the subcutaneously implanted power source of the neuronal stimulation apparatus. The means for transmitting the first neuronal stimulation signal may then transmit and/or generate a neuronal stimulation signal that indicates a relative position between the charging device and the apparatus that is suitable for wireless charging of the power source. Such a neuronal stimulation signal may either be binary, i.e. it may indicate whether the relative position is suitable for charging or not. Alternatively it may also be (quasi-) continuous allowing the individual to gradually optimize the charging position in order to maximize power transfer between the external charging device and the power source of the apparatus.

For instance, in some embodiments the system may further comprising means for transmitting a second neuronal stimulation signal indicative of an imminent transmission of the first neuronal stimulation signal intended for perception and/or interpretation by the individual and/or means for transmitting a third neuronal stimulation signal indicative of a completed transmission of the first neuronal stimulation signal.

In this way, a neuronal stimulation apparatus can first inform the user/patient that status information is to be transmitted. The user can then focus his attention to the imminent sensory percept to be elicited by the first neuronal stimulation signal. After the information carried by the first neuronal stimulation signal is perceived, the third neuronal stimulation signal may then inform the user/patient that no special attention focus is required anymore.

Further, in some embodiments, the means for determining the operational state of the apparatus may include a sensor, which may comprise one or more of the following:
  a. voltage, current and/or power measurement circuitry;
  b. a temperature sensor;
  c. a magnetic field sensor;
  d. signal analysis circuitry;
  e. a timer;
  f. connectivity measurement circuitry;
  g. circuit analysis circuitry;
  h. wireless packet data analysis circuitry;
  i. neuronal excitation measurement circuitry;
  j. power transfer measurement circuitry.

In this manner, the system may be enabled to determine various operational states of the apparatus and provide the user/patient with precise and detailed status information.

Further, the system described above may also comprise at least one of:
  a. means for generating the first and/or the second neuronal stimulation signal;
  b. an auxiliary power source;
  c. auxiliary digital signal processing circuitry;

d. auxiliary memory circuitry storing at least one neuronal stimulation signal or signal parameters for generating at least one neuronal stimulation signal;

e. signal multiplexing and/or switching circuitry;

f. an auxiliary signal amplifier for amplifying the first and/or the second neuronal stimulation signal;

g. magnetic and/or thermal shielding equipment;

h. means for obtaining the first and/or the second neuronal stimulation signal from memory circuitry or via a communication interface of the apparatus.

In this way, the system may provide redundant hard- and software components that provide the required functionalities for signaling the device status information via the neuronal stimulation signal to the individual. For instance, even if the primary battery of the neuronal stimulation apparatus is completely empty, the auxiliary power source could provide enough energy for generating and transmitting the required neuronal stimulation signal indicating to the individual that the primary battery is empty.

In some embodiments, the means for transmitting the first, second, and/or third neuronal stimulation signals may include transmitter circuitry comprised within the neuronal stimulation device. The transmitter circuitry may include one or more of a memory medium, a processor coupled to the memory medium, and/or a wireless interface configured to communicate via one or more wireless communication technologies (e.g., a short range wireless communication technology such as Bluetooth™ or WiFi, among other possibilities). In some embodiments, the transmitter circuitry may be configured to wirelessly communicate with the control device 130 to receive one or more of the first, second, and/or third neuronal stimulation signals, and may be further configured to provide one or more of the first, second, and/or third neuronal stimulation signals to the neuronal stimulation electrode 120.

Further, the means for generating the first neuronal stimulation signal may also comprise means for accessing a data storing means (e.g., a memory medium such as a non-transitory computer-readable memory medium) storing relations, specific for the individual, between a plurality of operational states and a plurality of corresponding neuronal stimulation signals.

In this manner, different device statuses can be encoded by different, patient specific neuronal stimulation signals that may be tailored to the patients neurophysiology and/or determined via a perceptual learning procedure associating different sensory percepts with different operational states of the apparatus.

Further, the first and/or the second neuronal stimulation signal may be characterized by a plurality of signal parameters such as a pulse frequency, a pulse polarity, a pulse shape, a pulse amplitude and/or a pulse width.

In particular, different combinations of signal parameters may correspond to different operational states of the apparatus to be indicated to the individual.

Further, in some embodiments, the neuronal stimulation means may comprise one of the following:

a. a brain stimulation electrode in particular a deep brain stimulation electrode;

b. a subdural stimulation electrode or subdural electrode array;

c. a subdural microwire or microwire array;

d. a transcranial stimulation device;

e. an unused contact of a neuromodulation electrode;

f. an artificial synapse;

g. an opto-neuronal interface device;

h. a chemical-neuronal interface device;

i. a neural surface mesh;

j. an injectable neural interface; and k. an artificial brain part, such as e.g. an artificial hippocampus.

In some embodiments, the first and/or the second neuronal stimulation signal may be adapted to elicit action potentials in at least one afferent axon targeting the sensory cortex of the individual. In particular, the first, the second and/or the third neuronal stimulation signal may be adapted to elicit a sensory percept in a portion of the cortex of the individual associated with a specific sensory modality.

Specifically, said portion of the cortex may be one or more of the following:

a. a somatosensory cortex area;

b. an auditory cortex area;

c. a visual cortex area;

d. an olfactory cortex area; and e. an entorhinal cortex area or components of the circuit of Papez.

By targeting afferent axons directly targeting the cortex of the individual a precise and fine-grained sensory specificity can be achieved for the different neuronal stimulation signals. For instance, different battery levels may be mapped to different areas within palm of the right hand of the patient by inducing action potentials in different sub-populations of axons targeting the sensory cortex of the right hand.

In another embodiment the present invention provides a neuronal stimulation apparatus comprising any of the systems described above.

For instance, the systems described above may be used with neuronal stimulation apparatuses such as:

a. a deep brain stimulation apparatus;

b. a neuromodulation apparatus;

c. a neuronal communication apparatus;

d. an electrical pacemaker apparatus;

e. a transcranial stimulation apparatus;

f. a brain-machine-interface apparatus;

g. a peripheral nervous system stimulator;

h. a vagus nerve stimulator;

i. a spinal cord stimulator;

j. a receptor (e.g. baroreceptor) or synapse stimulator or modulator;

k. a responsive neurostimulation device with integrated sensors;

l. a neuroprosthetic device;

In a further embodiment, the present invention provides a method for communicating an operational state of a neuronal stimulation apparatus to an individual, comprising: determining the operational state of the apparatus, transmitting a neuronal stimulation signal to a neuronal stimulation means of the individual adapted to elicit a sensory percept in the cortex of the individual, wherein the first neuronal stimulation signal is indicative of the determined operational state of the apparatus.

Such a method may further comprise a step of transmitting a second neuronal stimulation signal indicative of an imminent transmission of a first neuronal stimulation signal and/or a or a step of transmitting a third neuronal stimulation signal indicative of a completed transmission of the first neuronal stimulation signal.

As already discussed above, the operational state of the apparatus may comprise one or more of the following:

a. a fault state of the apparatus;

b. a charging state of a power source of the apparatus;

c. a normal operation state of the apparatus;

d. a maintenance state of the apparatus;
e. a connectivity state of the apparatus;
f. a communication state of the apparatus.

In addition, such a method may further comprise a step of: generating the first, the second and/or the third neuronal stimulation signal based on accessing a data storing means storing relations, specific for the individual, between a plurality of operational states and a plurality of corresponding neuronal stimulation signals.

Specifically, the specific relations may be based at least in part on one of the following:

a. conceptual learning data for the individual;
b. neuro-imaging data for the individual;
c. electrophysiological measurement data for the individual;
d. neuronal connectivity information for the individual;
e. electric field simulation data for the neuronal stimulation means of the individual;
f. neuronal excitability model data for the individual.

In this manner, even complex device status information such as a wireless connection signal quality indicator can be associated with corresponding sensory percepts that are specific for each individual.

In another embodiment, the present invention provides a computer program, comprising instructions to perform any of the methods described when executed by the signal processing circuitry of a neuronal stimulation apparatus such a one of the neuronal stimulation apparatuses mentioned above.

Figure 1:
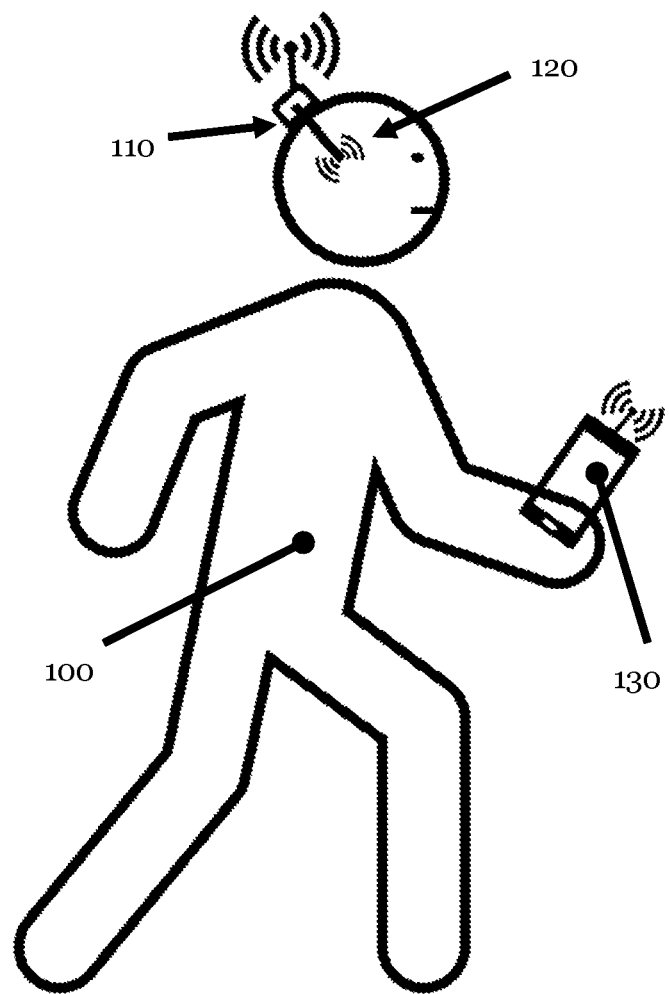
FIG. 1 is a diagram illustrating an individual operating a neuronal stimulation apparatus/device being equipped with a system according to an embodiment of the present invention.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

In the following, some exemplary embodiments of the present invention are described in more detail, with reference to neuronal stimulation and/or communication systems that can be interfaced with neuronal stimulation electrodes such as deep brain stimulation (DBS) electrodes. However, the systems provided by the present invention can also be used with different neuronal stimulation means (e.g. opto-neuronal, chemical-neuronal) that are capable to stimulate the sensory cortex of an individual e.g. via stimulating afferent axons targeting the sensory cortex.

While specific feature combinations are described in the following with respect to the exemplary embodiments of the present invention, it is to be understood that the disclosure is not limited to such embodiments. In other words, not all features have to be present for realizing the invention, and the embodiments may be modified by combining certain features of one embodiment with one or more features of another embodiment. Specifically, the skilled person will understand that features, components and/or functional elements of one embodiment can be combined with technically compatible features, components and/or functional elements of any other embodiment of the present invention.

Figure 3:
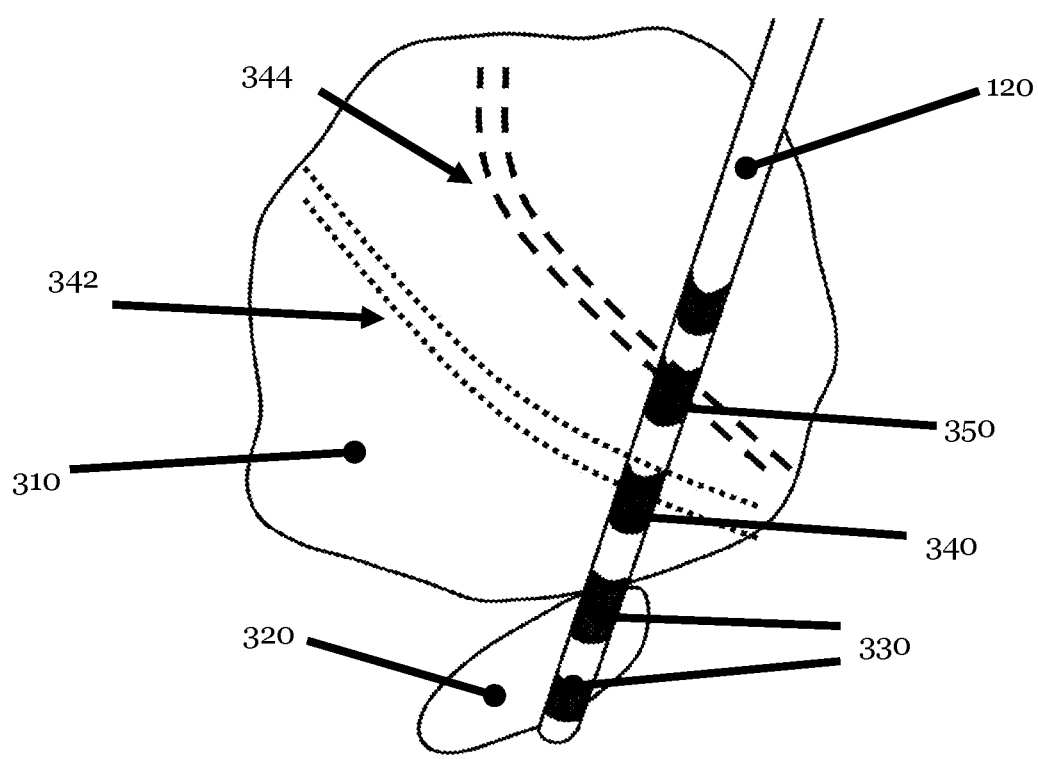
FIG. 3 is a diagram illustrating a therapeutic multi-contact neuromodulation electrode adapted for modulation of brain nuclei associated with PD. Unused contacts of the electrode can be used for stimulating afferent axons targeting the sensory cortex of an individual via a neuronal stimulation system according to an embodiment of the present invention.

FIG. 1 depicts an individual 100, e.g. a PD patient, that has been implanted with a neuronal stimulation electrode 120 such as a DBS electrode that may have multiple independently controllable electric contacts, as illustrated in FIG. 3 below. For instance, the neuronal stimulation electrode 120 may be already implanted into the brain of the individual 100 for the purpose of providing a neuromodulation therapy for certain PD symptoms such as tremor, dystonia and/or rigidity. However, the neuronal stimulation electrode 120 may also be implanted for other purposes such as for the purpose of neuronal communication and/or treatment of other movement impairments and neurological diseases such as Alzheimer's disease, epilepsy, depression, etc. Alternatively, the electrode 120 may also be implanted as a dedicated interface for the systems provided by the present invention.

The individual 100 may be further equipped with a neuronal stimulation device 110 that may be arranged on the head of the individual 100 or somewhere else on or in the vicinity of the body of the individual 100. The neuronal stimulation device 110 may be in wireless communication (e.g. via a Bluetooth™, WI-FI or similar wireless interface) with a control device 130, that may be implemented by a smartphone or a similar electronic information processing device. Depending on implementation details the systems provided by the present invention may be implemented via application specific hardware and/or software modules comprising circuitry and/or software instructions to implement a system according to the present invention.

The control device 130 may provide the individual with a user interface to adjust the neuronal stimulation signals and/or the neuromodulation therapy parameters applied via the neuronal stimulation device 110 and the neuronal stimulation electrode 120. The control device 130 may also provide connectivity to a packet based wireless large area network such as an LTE or 5G network. For instance, the individual 100 may use the control device 130 to adjust signal parameters such as a signal frequency, a pulse width, a pulse shape and/or a signal amplitude as well as for retrieving data from the interne.

Figure 2:
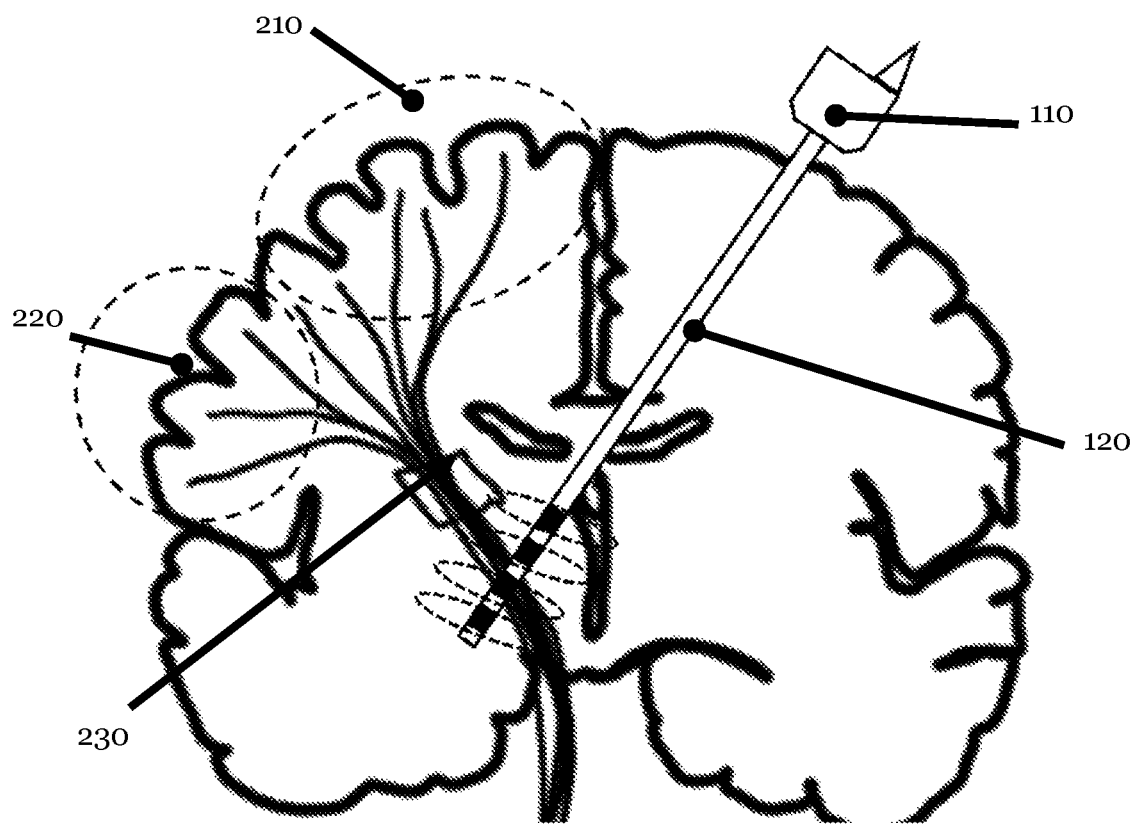
FIG. 2 is a diagram illustrating a neuronal stimulation electrode for stimulating afferent axons targeting the sensory cortex of an individual. The neuronal stimulation electrode can be interfaced with a neuronal stimulation system according to an embodiment of the present invention.

FIG. 2 depicts a diagram illustrating a neuronal stimulation electrode 120 for stimulating afferent axons 230 targeting sensory neurons in the cortex of a human brain. The afferent axons 230 may target different areas 210, 220 of the cortex that may be related to different sensory modalities (e.g. touch, temperature sense, vision, hearing, etc.) and/or different body regions (e.g. cochlea, retina, hand, tongue, foot etc.) from which the respective sensory modality is perceived by the respective area of the cortex. For instance, the cortical area 210 may be a somatosensory area of the right foot and the cortical area 220 may be a somatosensory area of the left hand.

The afferent axons 230 are connected via synapses (not shown) with their respective target neurons in the respective sensory area 210, 220. For instance, the axons 230 may be thalamocortical axons relaying sensory information from the thalamus to the cerebral cortex. The neuronal stimulation electrode 120 may comprises a plurality of independently controllable electric contacts (see FIG. 3 below) that may be arranged in the vicinity of a bundle of afferent axons 230 targeting the sensory areas 220 and 210 of the cerebral cortex.

In the illustrated example, the neuronal stimulation electrode 120 is connected to a neuronal stimulation device 110, which is adapted to apply neuronal stimulation signals to brain areas associated with certain neurophysiological symptoms and/or to the afferent axons 230, e.g. via independently controllable electric contacts of the neuronal stimulation electrode 120. In addition, the neuronal stimulation electrode 120 may further comprise a wireless interface for interfacing the neuronal stimulation device 110 with other systems that may which may be adapted to obtain and/or determine the waveform and/or signal parameters (e.g. pulse width, pulse shape, frequency, amplitude, number of pulses etc.) of the neuronal stimulation signal that is generated and applied by the neuronal stimulation device 110 to the afferent axons 230 via the stimulation electrode 120.

For instance, the neuronal stimulation system provided by the present invention may determine the waveform and/or signal parameters of the neuronal stimulation signal such that a desired sensory percept is elicited in a desired area of the sensory cortex of the individual. In some embodiments of the present invention, the cortex of the individual which is receiving the neuronal stimulation signal (i.e. via afferent action potentials of the stimulated afferent axons 230) may associate the corresponding sensory percept with several types of device status information such as a charging level of a battery, a hardware fault status, a communication status etc. For example, similar to learning how to understand Morse code, the individual may have previously participated in a learning procedure establishing an associative link between a given sensory percept elicited by a given neuronal stimulation signal and a corresponding device status (e.g. see FIGS. 7, 10, 12 and 13 below) that is to be communicated to the individual via the neuronal stimulation electrode 120.

In this approach no nuclei or neuron-rich grey matter are preferably targeted by the neuronal stimulation electrode 120 but preferably the axon-rich white matter of the brain, which contains the information transmitting pathways the brain uses for natural neural communication. In this manner, the present invention provides a white-matter computer-brain-interface (CBI), i.e. a system that generates and provides electrical signals the brain can interpret as meaningful input, e.g. as a charging level of the battery of the device 110. As discussed in section 3 above, such information may be provided by different types of measurement devices or sensors.

In other embodiments of the present invention, the neuronal stimulation electrode 120, the neuronal stimulation device 110 and/or the wireless interface may also be part of an integrated neuronal stimulation and/or communication system, e.g. if said components are customized for the intended application. For instance, a neuronal communication system may comprise of specialized communication software running on a multi-purpose information processing device such as a smartphone and a customized assembly of neuronal stimulation device 110 and stimulation electrode 120 which communicate with the multi-purpose communication device via a wireless interface using conventional wireless data transmission technology such as Wi-Fi, Bluetooth and/or NFC.

In other embodiments of the present invention the neuronal stimulation electrode 120 may be directly connected via wires to a neuronal stimulation system comprising a data processing system and a neuronal stimulation device similar to the neuronal stimulation device 110. In this case a wireless interface is not needed.

FIG. 3 depicts a multi-contact neuromodulation electrode 120 e.g. adapted for neuromodulation of the sub-thalamic nucleus 320 via electric contacts 330. The electrode 120 can also be used for stimulating afferent axons 342, 344 projecting from the thalamus 310 to the sensory cortex of an individual via a neuronal stimulation system according to the present invention. For example, neuronal stimulation signals may be provided by unused contacts 340, 350 of the neuromodulation electrode 120 that was implanted for a therapeutic purpose (e.g. neuromodulation of the subthalamic nucleus 320 via the therapeutic electric contacts 330) different from providing the neuronal stimulation signal to the afferent sensory axons 344, 342. For instance, the contacts that are not used for neuromodulation of the subthalamic nucleus 320 may be used to provide different kinds of device status information to the cortex of the individual. For example, such device status information may be signaled via a rhythmic sensory percept elicited by a neuronal stimulation signal applied to the axons 344 targeting a cortex area related to a touch sensation for instance in the left foot or the right hand.

In many cases, a DBS electrode 120 that is used as a neuromodulator, e.g. for treatment of symptoms of PD etc., is not always active and/or may comprise independently controllable contacts that are not required for achieving the therapeutic purpose. Thus, the neuromodulation electrode can also be used for applying neuronal stimulation signals provided by a system according to the present invention. For DBS electrodes, specifically, some of the electrode contacts located outside of the stimulation area of interest are not used. However, if implantation in e.g. the subthalamic nucleus 320 is conducted for the tip contacts 330 to control, for example, the primary PD symptoms more distal contacts 340, 350 could be used in combination with the above disclosed invention to communicate a device status information signal directly into the brain of the patient.

Figure 4:
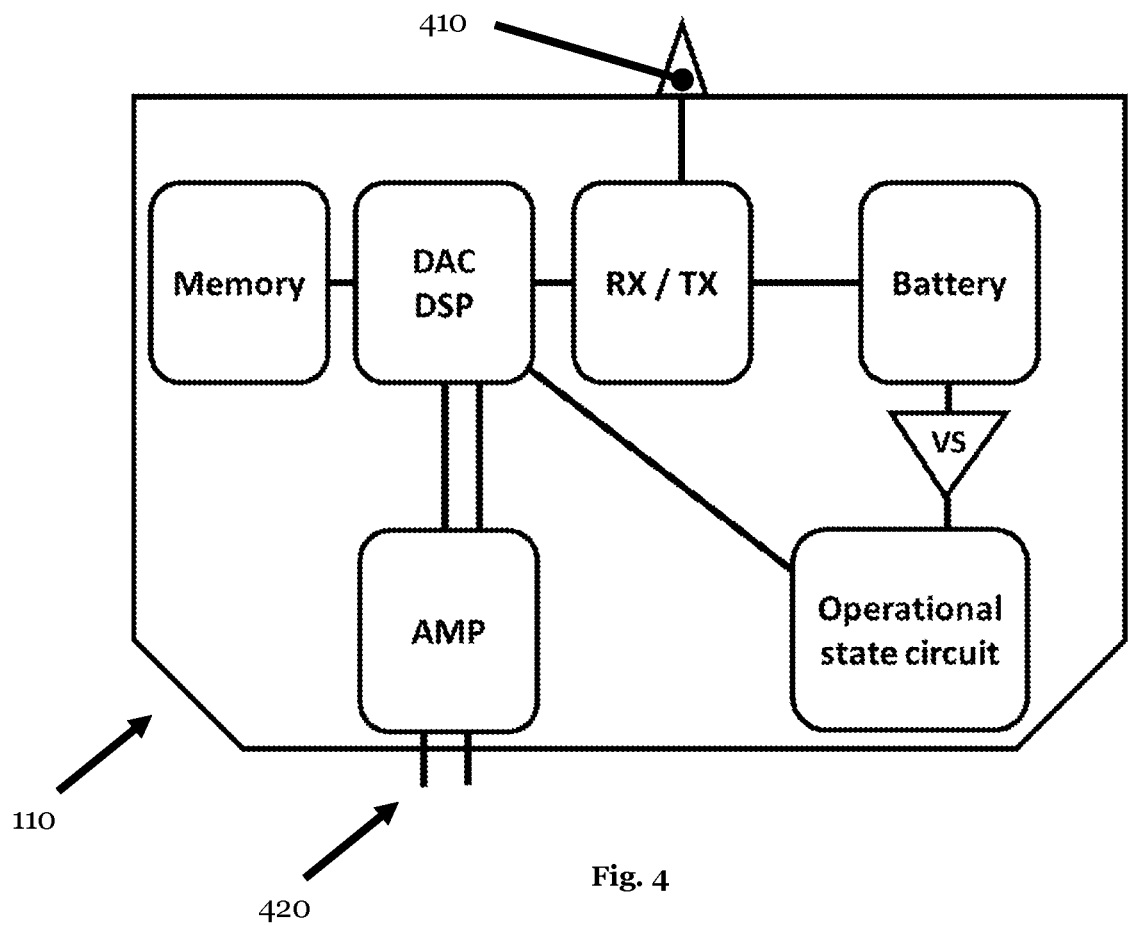
FIG. 4 is a block diagram of a neuronal stimulation apparatus/device comprising a system according to an embodiment of the present invention.

FIG. 4 depicts is a block diagram of a neuronal stimulation device 110 which can be used to apply neuronal stimulation signals to afferent axons 230 via a neuronal stimulation electrode such as the stimulation electrode 120 of FIGS. 1-3. The neuronal stimulation device 110 may comprise a wireless interface 410 for communicating with a remote control device 130 and/or a remote signal generation device which may be adapted to obtain, to determine, to select and/or to transmit a waveform and/or signal parameter of the neuronal stimulation signal to the neuronal stimulation device 110.

For instance, the neuronal stimulation neuronal stimulation device 110 may receive digital data packets specifying a desired neuronal therapy or communication signal via the wireless interface 410. Receiver (RX) circuitry may process (e.g. filter, amplify, mix, down-convert to baseband etc.) the received digital data packets specifying the waveform and/or the signal parameters (e.g. frequency, phase, pulse width, pulse amplitude, pulse shape, channel count, etc.) and feed the processed digital data packets to a digital signal processor (DSP) with may comprise an integrated digital-to-analog converter (DAC). The DSP then processes the digital data packets to generate one or more neuronal stimulation signals which may then be amplified and applied to a neuronal stimulation electrode such as electrode 120 of FIG. 2 and FIG. 3 by an output amplifier (AMP). For instance, the output AMP may be configured to drive four (or any other number) independently controllable electric contacts 330, 340, 350 of a stimulation electrode such as electrode 120 via the output wires 420.

In other embodiments, the DSP may receive the digital data packets specifying the neuronal stimulation signal also via a wire-based interface or directly from a collocated processing circuit (e.g. a CPU) which may be adapted to determine the waveform and/or signal parameters of a desired therapy or communication signal corresponding.

The neuronal stimulation apparatus 110 may further comprise an operational state circuit configured to monitor one or more types of device status information. For instance, the operational state circuit may be configured to monitor a voltage level of the battery of the device 110 via a voltage sensor (VS). The operational state circuit may be further configured for determining a battery charge level based on the output of the voltage sensor.

The operational state circuit may be further configured to provide an input signal to the DSP instructing the DSP to obtain, to determine, to select and/or to generate a neuronal stimulation signal that is to applied to a neuronal stimulation electrode via the output amplifier AMP and the output wires 420. For instance, in response to the input signal form the operational state circuit, the DPS may obtain signal parameters or the waveform of a neuronal stimulation signal from a memory device, wherein the neuronal stimulation signal corresponds to a device status information associated with the monitored battery charge level. For instance, the neuronal stimulation signal may correspond to a low-battery warning signal to be communicated to the individual using the neuronal stimulation device 110 (see FIG. 7 below).

The neuronal stimulation device 110 may further comprise at least one memory device operably connected to the DSP. The DSP and the memory may interact to determine a desired neuronal stimulation signal corresponding to a desired sensory percept such as the desired device status information to be communicated to the cortex of the individual.

For instance, the memory may contain a personalized communication library for the individual, the library storing relations between a plurality of device statuses and a plurality of corresponding neuronal stimulation signals.

Such a stimulation library can be calibrated for each individual through neuroimaging and/or individualized testing of the individual. Neuroimaging may first be used to identify theoretically possible ranges of activation for an individual stimulation electrode while individualized testing determines which points in the parameter space of stimulation signal parameters (for details see FIGS. 7, 10, 12 and 13 below) can be perceived and decoded by the cortex of the individual. It should be emphasized that conscious individualized testing of an individual is merely one specific example how to generate the individualized relations stored in the memory. In other embodiments such relations may also be obtained from unconscious patients, e.g. through the non-invasive observation of corresponding functional MRI responses on the somatosensory cortex or EEG recordings.

Further, once or while the communication library (i.e. the plurality of relations stored in the memory) is established or is being established for an individual a specific training procedure can be executed (again not necessarily in a conscious individual). As long as the cortex of the individual responds to classical conditioning, pair learning can be executed. In the context of the present invention, such a pair consists of a given sensory percept corresponding to a given neuronal stimulation signal and a device status to be associated with said given sensory percept and the corresponding neuronal stimulation signal.

Importantly, the type of information to be conveyed via the neuronal stimulation device 110 whether it is a battery status signal, a communication status signal or a hardware fault status signal etc. can be chosen freely. Any information or message which can be broken down into message blocks (i.e. pieces of conceptual information that can be decoded by the cortex of an individual) can be transmitted. This includes continuous signals such as signals needed for a (quasi-) continuous battery charge indication (see FIG. 12 below) or other sensor measurement signals.

Learning paradigms for continuous signals deviate from classical conditioning, since they involve more interactive training scenarios where utilization of the signal is a relevant success factor (e.g. orientation in an artificial virtual environment using the input signal). Continuous signals (e.g. intensity) also deviate from signal configurations for messages containing sequentially delivered message blocks. In the case of continuous signals, intensity might be coded via either pulse width or frequency variations (or combinations of the two; see FIGS. 12 and 13 below), while not varying the location and target areas in the sensory cortex targeted by the recruited axon fibers.

Figure 5:
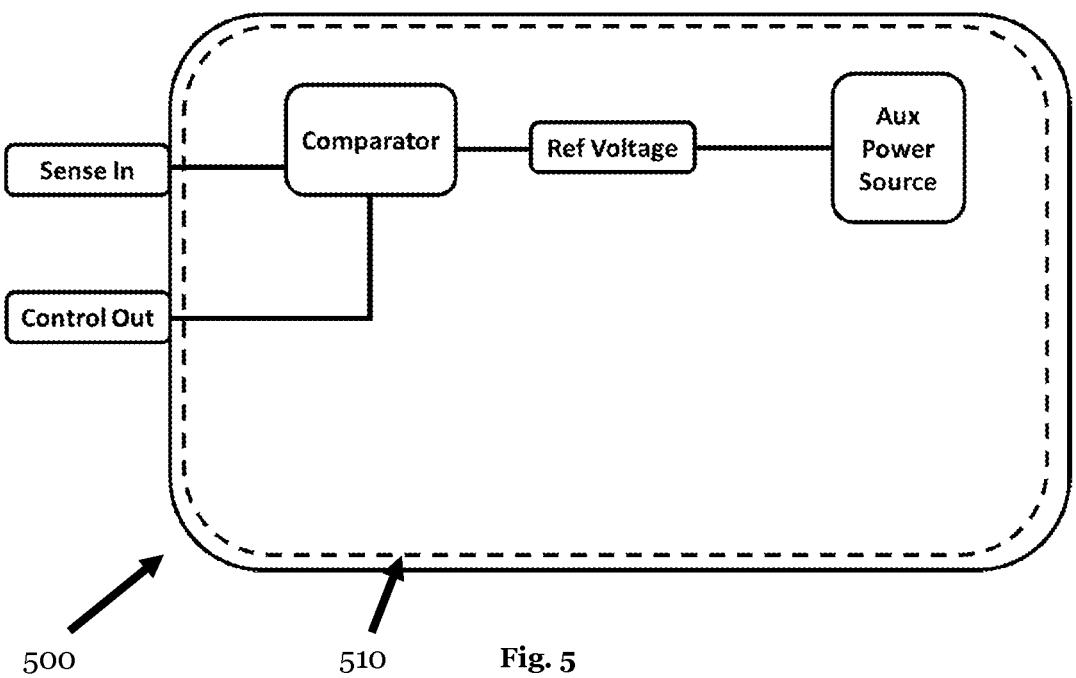
FIG. 5 is a block diagram of an operational state circuit that may be part of or be used with a systems according to an embodiment of the present invention.

FIG. 5 depicts a block-type circuit diagram of an exemplary operational state circuit 500. The operational state circuit may comprise an input terminal (Sense In) e.g. connected to the output of a voltage sensor VS (see FIG. 4 above) and an output terminal (Control Out) e.g. connected to an input of a DSP (see FIG. 4 above). The operational state circuit may further comprise an auxiliary power source and a comparator circuit (e.g. a standard OP-AMP circuit) that compares the input signal being applied to Sense In to a reference voltage (Ref voltage). If the input voltage signal falls below (above) the reference voltage the comparator produces an output signal that is applied via Control Out to the DSP. In response to the input signal from the operational state circuit 500, the DPS may then obtain a waveform (or signal parameters specifying a waveform) of a neuronal stimulation signal such as a pulse train signal from memory, wherein the neuronal stimulation signal corresponds to a device status information associated with the monitored battery charge level. For instance, the neuronal stimulation signal may correspond to a low-battery warning signal to be communicated to the individual using the neuronal stimulation device 110.

The operational state circuit 500 may further comprise magnetic shielding equipment 510 protecting the circuit elements of the operational state circuit, thereby increasing the reliability and fail-safe operation of the operational state circuit 500.

Figure 6:
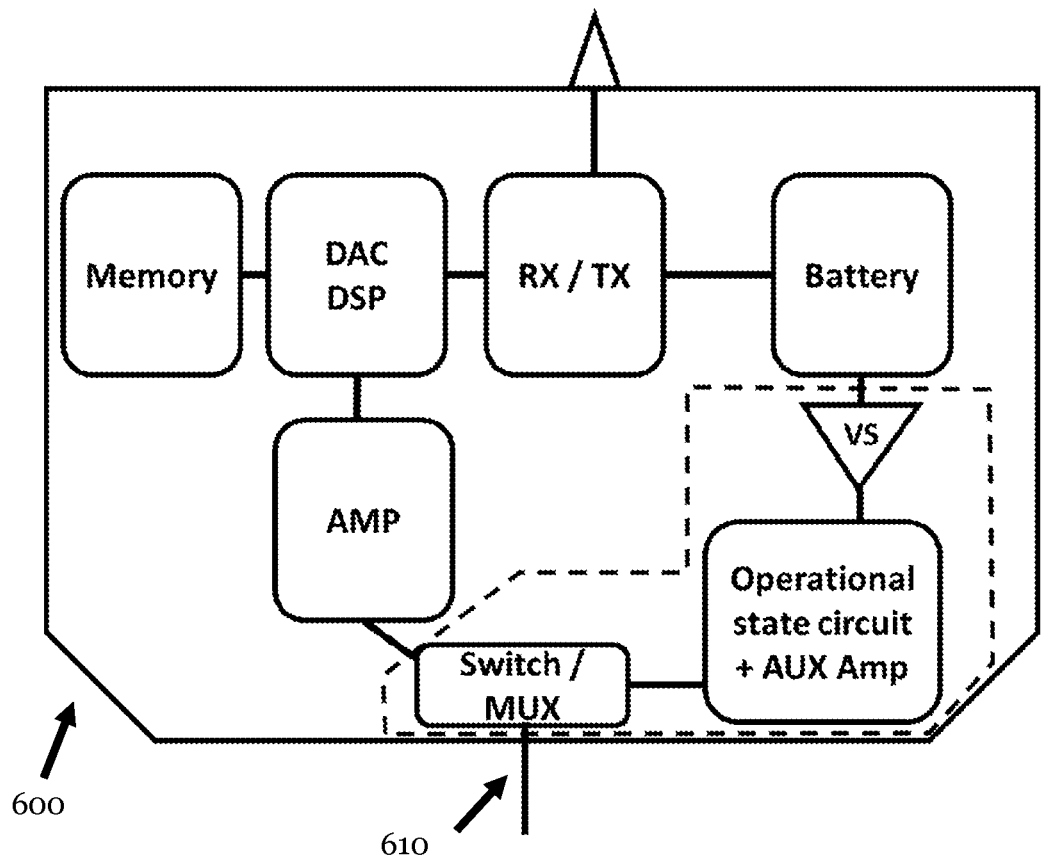
FIG. 6 is a block diagram of a neuronal stimulation apparatus/device comprising a system according to an embodiment of the present invention.

FIG. 6 depicts is a block diagram of a neuronal stimulation device 600 that is similar to the neuronal stimulation device of FIG. 4 discussed above. In addition to the circuit components discussed above, the neuronal stimulation device 600 comprises a switch or multiplexing circuitry (Switch/MUX) that allows to apply a neuronal stimulation signal generated by the operational state circuit (which comprises an auxiliary signal amplifier) to the output wires 610 that connect to a neuronal stimulation electrode, such as the multi-contact electrode discussed above with reference to FIGS. 2 and 3.

In the example of FIG. 6 the operational state circuit also comprises means to generate a neuronal stimulation signal corresponding to the monitored battery charge status. In this way, the battery charge status signal can even be transmitted to the brain of the individual without involving the primary signal processing circuitry of the device 600 that may not be functional anymore. Similar to the operational state circuit of FIG. 5 also the device 600 may further comprise magnetic shielding equipment protecting the voltage sensor (VS) the operational state circuit and/or the switch or multiplexing circuit.

Figure 7:
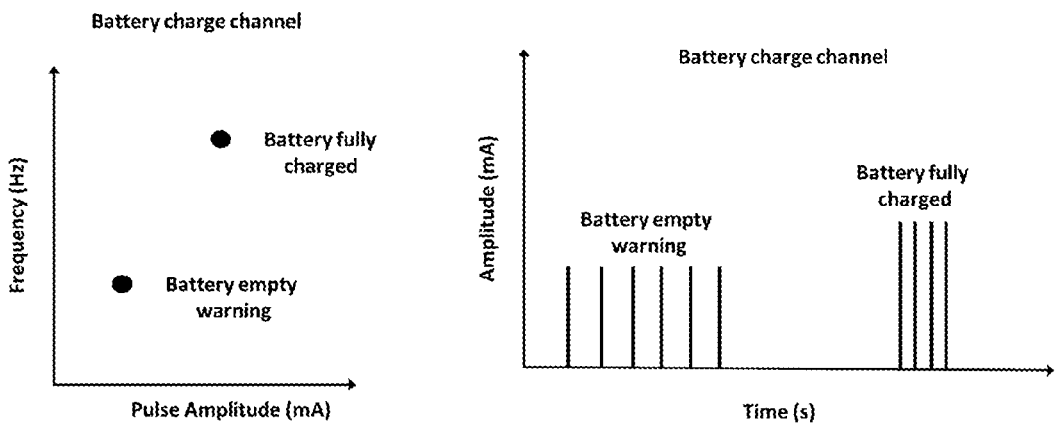
FIG. 7 is a diagram illustrating how a binary battery charge status channel can be implemented using a neuronal stimulation system according to an embodiment of the present invention.

FIG. 7 illustrates how embodiments of the present invention can be used to establish a binary battery charge status channel to the to the cortex of an individual and to use said battery charge status channel to provide a indicate to the individual to recharge the battery.

For instance, two different battery charge status signals may be encoded by providing a pulse train signal via a neuronal stimulation interface and system as discussed above. Such a pulse train (being characterized by signal parameters such as pulse width, pulse frequency, pulse shape and/or pulse amplitude) may elicit a periodic/rhythmic sensory percept in the targeted area of the sensory cortex of the individual. For instance, such a pulse train signal may be configured to elicit a periodically appearing tough sensation in the palm of the right hand or in a leg of the individual. For instance, a battery empty warning signal may be encoded by choosing a certain combination of pulse train parameters such as a combination of a relatively lower pulse frequency and a relatively small pulse amplitude as indicted in FIG. 7. Similarly, a higher pulse frequency and larger amplitude may be associated with a signal indicating that the battery is fully charged.

Figure 8:
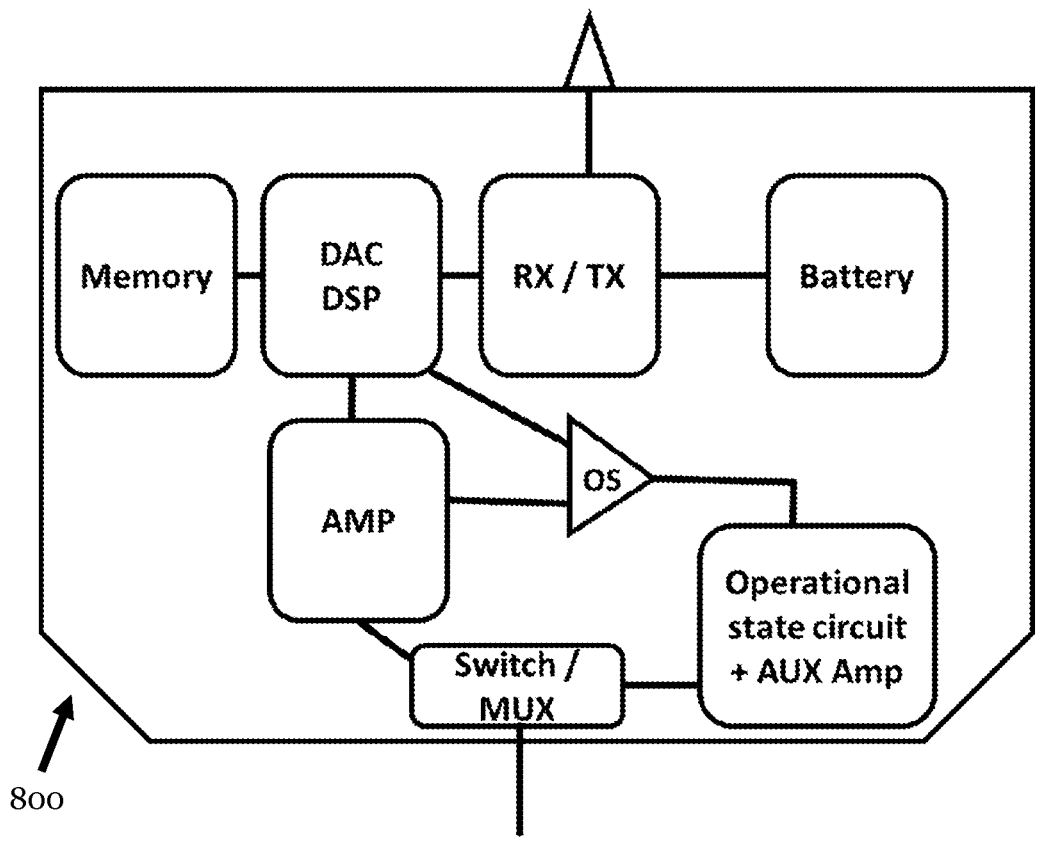
FIG. 8 is a block diagram of a neuronal stimulation apparatus comprising a system according to an embodiment of the present invention adapted to monitor and signal operational status information.

FIG. 8 illustrates a further example of a neuronal stimulation device being equipped with a system according to the present invention. Similar to the neuronal stimulation devices 110 and 600 of FIGS. 4 and 6 the device 800 depicted in FIG. 8 comprises an operational state circuit adapted to monitor one or more types of device status information. For instance, the operational state circuit may receive input signals from one or more operational state sensors (OS) monitoring whether certain primary circuit elements (such as the DSP of the output amplifier) of the device 800 operate within specified operation parameter ranges. For instance, the OS may monitor a temperature of the DSP and/or of the AMP to inform the individual when these components may overheat.

Figure 9:
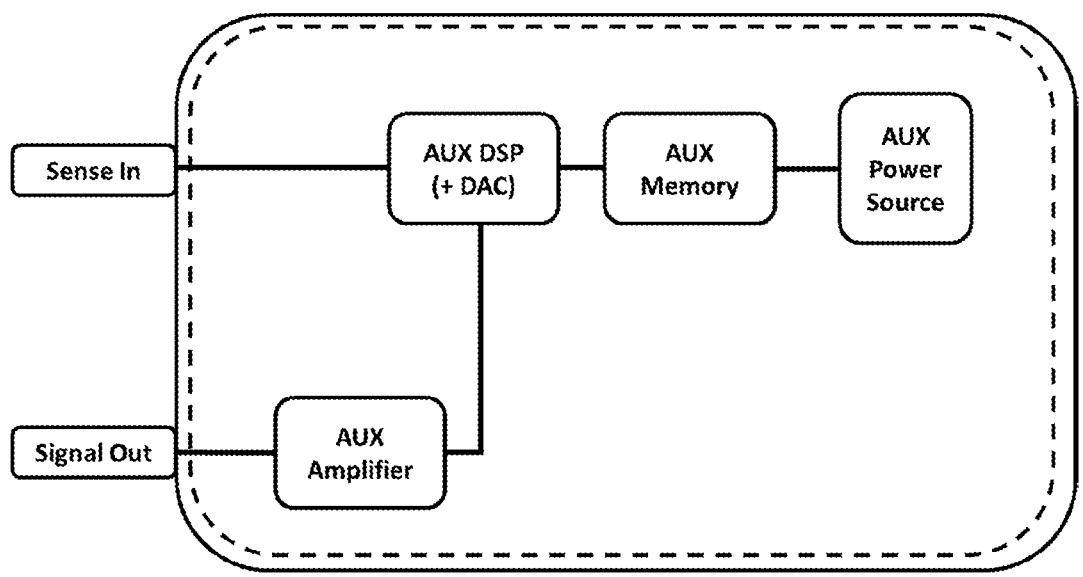
FIG. 9 is a block diagram of an operational state circuit that may be part of or be used with a systems according to an embodiment of the present invention.

FIG. 9 depicts another example of an operational state circuit 900 that may be used in or with a system according to the present invention. The operational state circuit 900 comprises all circuitry necessary for generating and transmitting neuronal stimulation signals corresponding to various kinds of device status information. For instance, a auxiliary DSP (AUX DSP) may receive various kinds of input signal via Sense In such as a signal indicating that the primary DPS has been switches off due to overheating.

In this case, the DSP retrieves a waveform or signal parameters specifying a waveform of a neuronal stimulation signal from an auxiliary memory (AUX Memory) device, the retrieved neuronal stimulation signal indicating a fault state of the neuronal stimulation device to the individual. In this way, the individual can even be informed of a critical fault of the neuronal stimulation device, even if said critical fault would otherwise prevent the neuronal stimulation device to generate neuronal stimulation signals.

Figure 10:
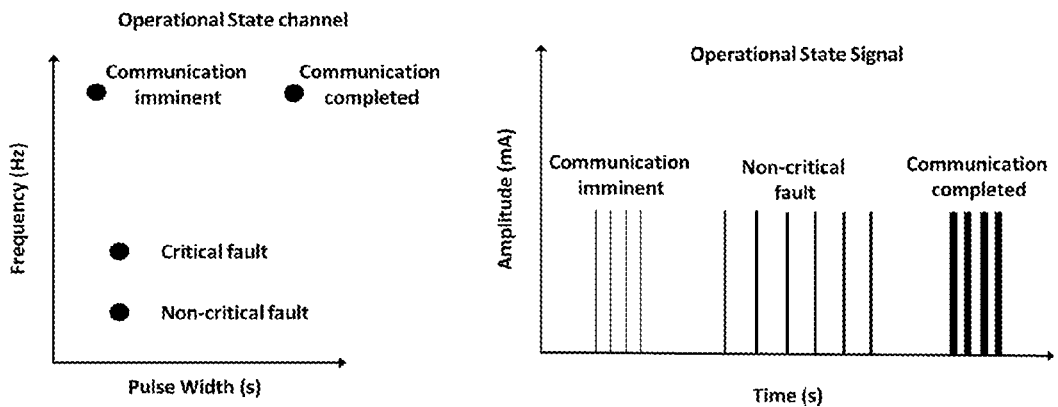
FIG. 10 is a diagram illustrating how a communication status signal and a device fault signal can be implemented using a neuronal stimulation system according to an embodiment of the present invention.

FIG. 10 illustrates how embodiments of the present invention can be used to establish a perceptive communication channel to the cortex of an individual for signaling both, a communication status and a fault status of a neuronal stimulation device.

A first set of pulse frequencies and pulse widths may be used to signal to the individual that communication of the actual device status information is imminent (e.g. will commence soon) or completed. In this way it can be ensured that the individual using such a neuronal stimulation device focusses his attention to the device status information to be communicated. A second set of set of pulse frequencies and pulse widths may then be used to signal the actual device status information (or any other kind of information to be communicated to the individual).

Figure 11:
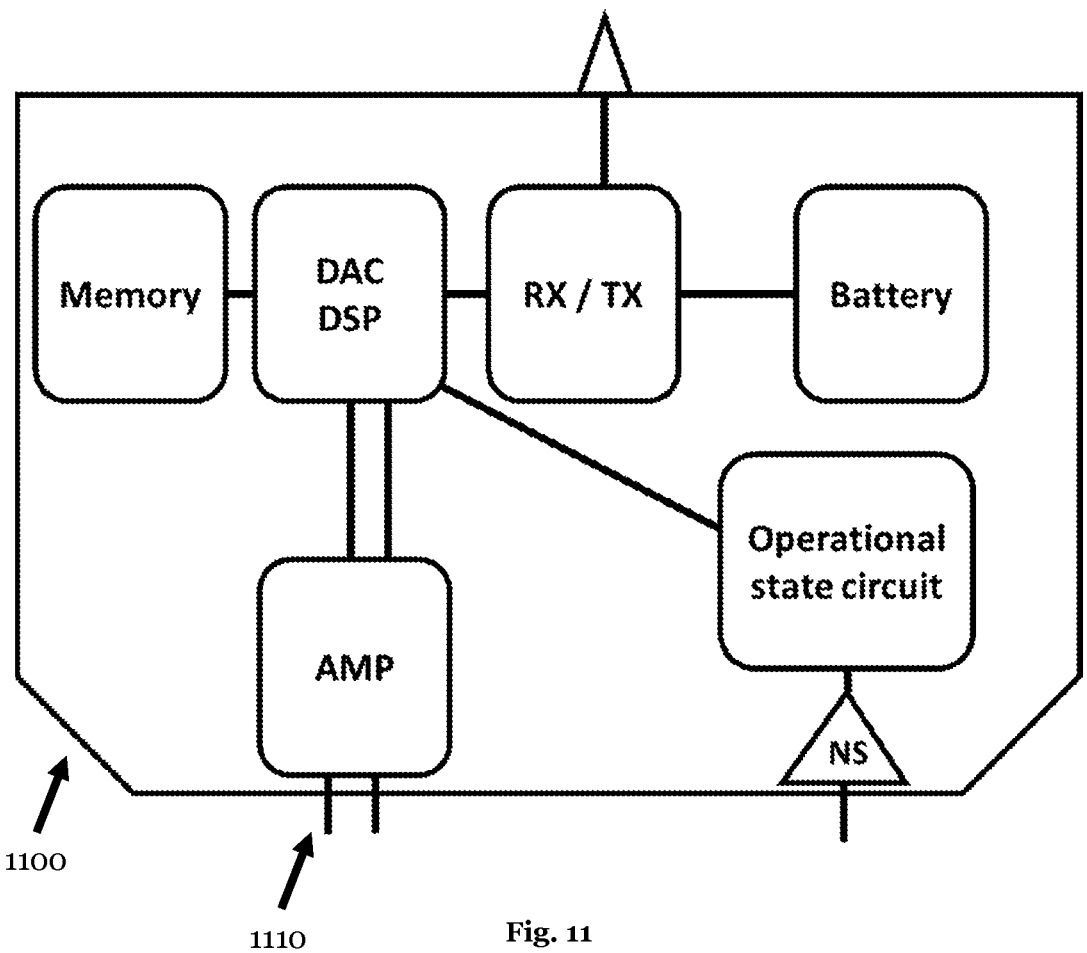
FIG. 11 is a block diagram of a neuronal stimulation device/apparatus comprising a system according to an embodiment of the present invention configured for monitoring whether the output signals of neuronal stimulation device are within specified parameter ranges.

FIG. 11 shows another example of a neuronal stimulation device that is similar to the devices discussed above for FIGS. 4, 6 and 8. In this example, the operational state circuit is adapted to receive monitoring signals from a neuronal signal sensor (NS) that monitors the primary neurostimulation signals outputted via the output vires 1110 (e.g. a neuromodulation signal for treatment of PD). For instance, the NS may be connected to a reference electrode attached to the skin or the skull (e.g. sub- or supra-dural) of the individual using the device 1100. The NS may generate a voltage signal that is related to the neuronal stimulation signals applied via wires 1110. The operational state circuit may be configured to use the voltage signal generated by the NS to determine whether the signal parameters of the primary neuronal stimulation signals are still within specified parameter ranges required for proper functioning of the device 1100. For instance, if the voltage signal of the NS indicates that the signal amplitude and/or frequency of the primary neuronal stimulation signal is to low for achieving the desired therapeutic purpose, the operational state circuit may cause the DSP to generate a neuronal stimulation signal to be applied via wires 1110 to a neuronal stimulation electrode indicating to the treated individual that maintenance of the device 1100 is required.

Figure 12:
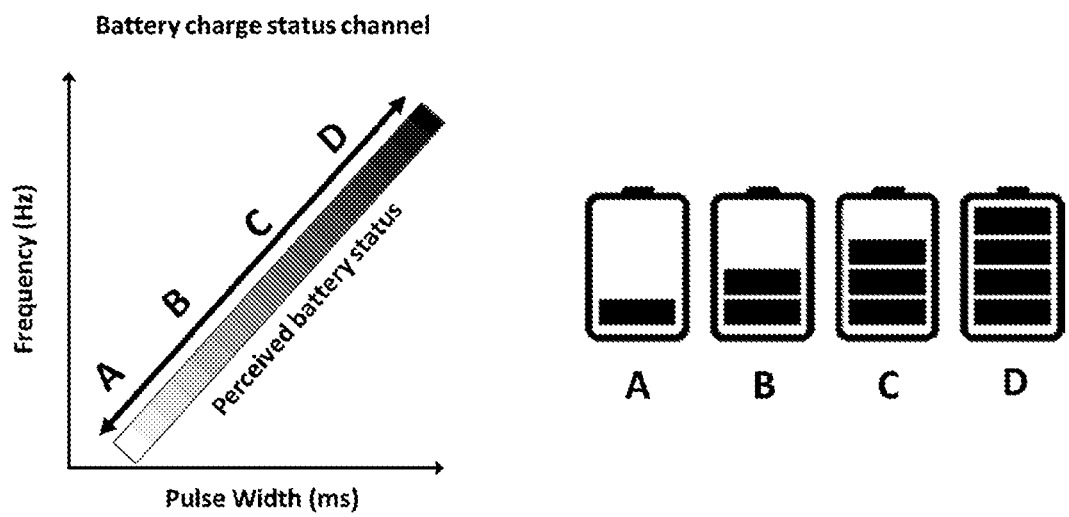
FIG. 12 is a diagram illustrating how a (quasi-) continuous communication channel for signaling a battery charging level can be implemented using a neuronal stimulation system according to an embodiment of the present invention.
Figure 13:
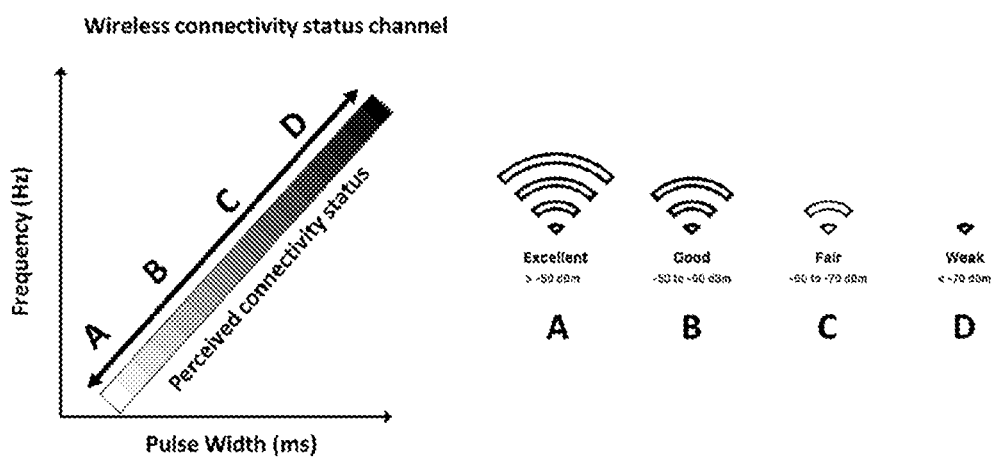
FIG. 13 is a diagram illustrating how a (quasi-) continuous communication channel for signaling a wireless connectivity status can be implemented using a neuronal stimulation system according to an embodiment of the present invention.

FIG. 12 illustrates how a (quasi-) continuous neuronal communication channel can be implemented the may be used for signaling the charging level of a battery directly to the brain of an individual.

The measurement signal of a battery voltage sensor may be used to determine a neuronal stimulation signal to be applied to at least one afferent axon targeting at least one sensory neuron in the cortex of the individual, wherein the determined neuronal stimulation signal corresponds to the battery charge level that is communicated to the individual.

As shown in FIG. 12, battery charge level may be encoded by a combination of signal parameters such as pulse width and pulse frequency of a pulse train signal. In the example shown in FIG. 12 a low frequency pulse train having a short pulse width (A) corresponds to an almost empty battery (A) whereas a high frequency pulse train having a long pulse width (D) corresponds to a fully charged battery (D).

FIG. 12 illustrates how a (quasi-) continuous neuronal communication channel can be implemented the may be used for signaling the signal quality of a wireless communication interface of a neuronal stimulation device.

For instance, the measurement signal of a signal strength sensor may be used to determine a neuronal stimulation signal to be applied to at least one afferent axon targeting at least one sensory neuron in the cortex of the individual, wherein the determined neuronal stimulation signal corresponds to the signal strength of a wireless reference signal level that is communicated to the individual.

As shown in FIG. 12, the wireless signal strength may be encoded by a combination of signal parameters such as pulse width and pulse frequency of a pulse train signal. In the example shown in FIG. 12 a low frequency pulse train having a short pulse width (A) corresponds to a strong signal (A) whereas a high frequency pulse train having a long pulse width (D) corresponds to a very weak wireless signal quality (D).

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A system for communicating an operational state of a neuronal stimulation apparatus to an individual, the system comprising:
   a sensor configured to determine the operational state of the neuronal stimulation apparatus;
   a non-transitory memory medium storing signal parameters of one or more neuronal stimulation signals indicative of one or more operational states of the neuronal stimulation apparatus;
   signal processing circuitry for generating a first neuronal stimulation signal based on a set of signal parameters retrieved from the non-transitory memory medium corresponding to the determined operational state of the neuronal stimulation apparatus; and
   transmitter circuitry configured to transmit the first neuronal stimulation signal to a neuronal stimulation device of the individual,
   wherein the first neuronal stimulation signal is adapted to elicit a specific first sensory percept in a portion of the cortex of the individual that is associated with a specific sensory modality; and
   wherein the first neuronal stimulation signal is indicative, via the specific first sensory percept, of the determined operational state of the neuronal stimulation apparatus.

2. The system of claim 1, wherein the transmitter circuitry is further configured to perform one or both of:
   prior to transmitting the first neuronal stimulation signal, transmitting a second neuronal stimulation signal adapted to elicit a specific second sensory percept in a portion of the cortex of the individual, indicative of imminent transmission of the first neuronal stimulation signal and intended for one or both of perception and interpretation by the individual; and
   after transmitting the first neuronal stimulation signal, transmitting a third neuronal stimulation signal adapted to elicit the specific second sensory percept or a specific third sensory percept in a portion of the cortex of the individual, indicative of completed transmission of the first neuronal stimulation signal.

3. The system of claim 1, the system further comprising one or more of:
   circuitry for generating the first neuronal stimulation signal;
   an auxiliary power source;
   auxiliary digital signal processing circuitry;
   auxiliary memory circuitry storing at least one neuronal stimulation signal or signal parameters for generating at least one neuronal stimulation signal;
   signal multiplexing and/or switching circuitry;
   an auxiliary signal amplifier for amplifying the first neuronal stimulation signal;
   magnetic and/or thermal shielding equipment; and
   circuitry configured to obtain the first neuronal stimulation signal from the auxiliary memory circuitry or via a communication interface of the apparatus.

4. The system of claim 1, wherein the first neuronal stimulation signal is characterized by one or more a plurality of signal parameters, wherein the one or more plurality of signal parameters comprises one or more of a pulse frequency, a pulse polarity, a pulse shape, a pulse amplitude or a pulse width.

5. The system of claim 4, wherein different combinations of the one or more signal parameters correspond to different operational states of the neuronal stimulation apparatus.

6. The system of claim 1, wherein the first neuronal stimulation signal is adapted to elicit action potentials in at least one afferent axon targeting the sensory cortex of the individual.

7. The system of claim 1, wherein the portion of the cortex comprises one or more of the following: a somatosensory cortex area; an auditory cortex area; a visual cortex area; an olfactory cortex area; an entorhinal cortex area or components of the circuit of Papez.

8. A neuronal stimulation apparatus comprising:
   a sensor configured to determine an operational state of the neuronal stimulation apparatus;

a non-transitory memory medium storing signal parameters of one or more neuronal stimulation signals indicative of one or more operational states of the neuronal stimulation apparatus;

signal processing circuitry for generating a first neuronal stimulation signal based on a set of signal parameters retrieved from the non-transitory memory medium corresponding to the determined operational state of the neuronal stimulation apparatus; and transmitter circuitry configured to transmit the first neuronal stimulation signal to a neuronal stimulation device of the individual, wherein the first neuronal stimulation signal is adapted to elicit a specific first sensory percept in a portion of the cortex of the individual that is associated with a specific sensory modality, wherein the first neuronal stimulation signal is indicative, via the specific first sensory percept, of the determined operational state of the neuronal stimulation apparatus.

9. The neuronal stimulation apparatus of claim 8, wherein the transmitter circuitry is further configured to perform one or both of:

prior to transmitting the first neuronal stimulation signal, transmitting a second neuronal stimulation signal adapted to elicit a specific second sensory percept in a portion of the cortex of the individual, indicative of imminent transmission of the first neuronal stimulation signal and intended for one or both of perception and interpretation by the individual; and after transmitting the first neuronal stimulation signal, transmitting a third neuronal stimulation signal adapted to elicit the specific second sensory percept or a specific third sensory percept in a portion of the cortex of the individual, indicative of completed transmission of the first neuronal stimulation signal.

10. The neuronal stimulation apparatus of claim 8, wherein the first neuronal stimulation signal is characterized by one or more a plurality of signal parameters, wherein the one or more plurality of signal parameters comprises one or more of a pulse frequency, a pulse polarity, a pulse shape, a pulse amplitude or a pulse width.

11. The neuronal stimulation apparatus of claim 10, wherein different combinations of the one or more signal parameters correspond to different operational states of the neuronal stimulation apparatus.

12. The neuronal stimulation apparatus of claim 8, wherein the first neuronal stimulation signal is adapted to elicit action potentials in at least one afferent axon targeting the sensory cortex of the individual.

13. The neuronal stimulation apparatus of claim 8, wherein the portion of the cortex comprises one or more of the following: a somatosensory cortex area; an auditory cortex area; a visual cortex area; an olfactory cortex area; an entorhinal cortex area or components of the circuit of Papez.

14. A non-transitory computer-readable memory medium comprising program instructions which, when executed by a processor cause a neuronal stimulation device to:

determine an operational state of the neuronal stimulation device;

access a non-transitory memory medium storing signal parameters of one or more neuronal stimulation signals indicative of one or more operational states of the neuronal stimulation device and retrieve a set of signal parameters based on the determined operational state;

generate, based on the retrieved set of signal parameters, a first neuronal stimulation signal indicative of the determined operational state of the neuronal stimulation apparatus;

transmit the first neuronal stimulation signal to the neuronal stimulation device of an individual, wherein the first neuronal stimulation signal is adapted to elicit a specific first sensory percept in a portion of the cortex of the individual that is associated with a specific sensory modality, and wherein the first neuronal stimulation signal is indicative, via the specific first sensory percept, of the determined operational state of the neuronal stimulation apparatus.

15. The non-transitory computer-readable memory medium of claim 14, wherein the program instructions are further executable by the processor to cause the neuronal stimulation device to perform one or both of:

prior to transmitting the first neuronal stimulation signal, transmitting a second neuronal stimulation signal adapted to elicit a specific second sensory percept in a portion of the cortex of the individual, indicative of imminent transmission of the first neuronal stimulation signal and intended for one or both of perception and interpretation by the individual; and after transmitting the first neuronal stimulation signal, transmitting a third neuronal stimulation signal adapted to elicit the specific second sensory percept or a specific third sensory percept in a portion of the cortex of the individual, indicative of completed transmission of the first neuronal stimulation signal.

16. The non-transitory computer-readable memory medium of claim 14, wherein the first neuronal stimulation signal is characterized by one or more a plurality of signal parameters, wherein the one or more plurality of signal parameters comprises one or more of a pulse frequency, a pulse polarity, a pulse shape, a pulse amplitude or a pulse width.

17. The non-transitory computer-readable memory medium of claim 15, wherein different combinations of the one or more signal parameters correspond to different operational states of the neuronal stimulation apparatus.

18. The non-transitory computer-readable memory medium of claim 14, wherein the first neuronal stimulation signal is adapted to elicit action potentials in at least one afferent axon targeting the sensory cortex of the individual.

19. The non-transitory computer-readable memory medium of claim 14, wherein the portion of the cortex comprises one or more of the following: a somatosensory cortex area; an auditory cortex area; a visual cortex area; an olfactory cortex area; an entorhinal cortex area or components of the circuit of Papez.

20. A method for communicating an operational state of a neuronal stimulation apparatus to an individual, the method comprising:

determining an operational state of the neuronal stimulation apparatus;

accessing a non-transitory memory medium storing signal parameters of one or more neuronal stimulation signals indicative of one or more operational states of the neuronal stimulation device and retrieving a set of signal parameters based on the determined operational state;

generating, based on the retrieved set of signal parameters, a first neuronal stimulation signal indicative of the determined operational state of the neuronal stimulation apparatus;

transmitting the first neuronal stimulation signal to a neuronal stimulation device of an individual, wherein the first neuronal stimulation signal is adapted to elicit a specific first sensory percept in a portion of the cortex of the individual that is associated with a specific sensory modality, wherein the first neuronal stimulation signal is indicative, via the specific first sensory percept, of the determined operational state of the neuronal stimulation apparatus.

21. The method of claim 20, the method further comprising one or both of:

prior to transmitting the first neuronal stimulation signal, transmitting a second neuronal stimulation signal adapted to elicit a specific second sensory percept in a portion of the cortex of the individual, indicative of imminent transmission of the first neuronal stimulation signal and intended for one or both of perception and interpretation by the individual; and after transmitting the first neuronal stimulation signal, transmitting a third neuronal stimulation signal adapted to elicit the specific second sensory percept or a specific third sensory percept in a portion of the cortex of the individual, indicative of completed transmission of the first neuronal stimulation signal.

22. The method of claim 20, wherein the first neuronal stimulation signal is characterized by one or more a plurality of signal parameters, wherein the one or more plurality of signal parameters comprises one or more of a pulse frequency, a pulse polarity, a pulse shape, a pulse amplitude or a pulse width.

23. The method of claim 22, wherein different combinations of the one or more signal parameters correspond to different operational states of the neuronal stimulation apparatus.

24. The method of claim 20, wherein the first neuronal stimulation signal is adapted to elicit action potentials in at least one afferent axon targeting the sensory cortex of the individual.

25. The method of claim 20, wherein the portion of the cortex comprises one or more of the following: a somatosensory cortex area; an auditory cortex area; a visual cortex area; an olfactory cortex area; an entorhinal cortex area or components of the circuit of Papez.

* * * * *